United States Patent [19]

Pastor et al.

[11] Patent Number: 4,783,495
[45] Date of Patent: Nov. 8, 1988

[54] (HYDROXYPHENYL) SILANE STABILIZERS

[75] Inventors: Stephen D. Pastor, Basle, Switzerland; Edward T. Hessell, Rochester, N.Y.

[73] Assignee: Ciba-Geigy Corporation, Ardsley, N.Y.

[21] Appl. No.: 123,470

[22] Filed: Nov. 20, 1987

[51] Int. Cl.$^4$ .............. C07F 7/18; C07F 7/12; C07F 7/08; C08K 5/54
[52] U.S. Cl. .................. 524/263; 524/265; 556/443; 556/449; 556/463; 556/484; 556/486
[58] Field of Search .......... 524/265, 263; 556/486, 556/449, 463, 484, 443

[56] References Cited

U.S. PATENT DOCUMENTS

| | | | |
|---|---|---|---|
| 2,611,777 | 9/1952 | Speier | 556/449 |
| 3,137,720 | 6/1964 | Cooper | 556/449 |
| 3,491,137 | 1/1970 | Zaweski et al. | 556/449 |
| 3,586,705 | 6/1971 | Owen et al. | 556/449 |
| 4,132,702 | 1/1979 | Schmidt et al. | 556/449 |
| 4,274,996 | 6/1981 | Hawley | 524/263 |
| 4,283,505 | 8/1981 | Kleeberg et al. | 556/486 |
| 4,430,235 | 2/1984 | Chu et al. | 556/449 |
| 4,582,870 | 4/1986 | Spivack et al. | 524/265 |
| 4,636,573 | 1/1987 | Pastor et al. | 524/265 |
| 4,724,248 | 2/1988 | Dexter et al. | 524/265 |

FOREIGN PATENT DOCUMENTS

| | | | |
|---|---|---|---|
| 60-245643 | 5/1984 | Japan | 524/265 |
| 61-100587 | 5/1986 | Japan . | |
| 865871 | 9/1981 | U.S.S.R. | 556/449 |
| 1011649 | 4/1983 | U.S.S.R. | 556/486 |
| 1196366 | 12/1985 | U.S.S.R. | 556/449 |

OTHER PUBLICATIONS

Wilson, G. R. et al.—J. Org. Chem. 24, No. 11, Nov. 1959, pp. 1717–1719.

Primary Examiner—Veronica P. Hoke
Attorney, Agent, or Firm—Harry Falber

[57] ABSTRACT ((Hydroxyphenyl)silane derivatives of the formula

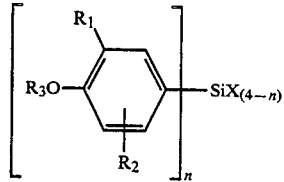

are effective in stabilizing organic materials against oxidative, thermal and actinic degradation, said derivatives being particularly effective as process stabilizers in organic materials containing phenolic antioxidants.

20 Claims, No Drawings

(HYDROXYPHENYL) SILANE STABILIZERS

Organic polymeric materials such as plastics and resins are subject to thermal, oxidative and photodegradation. A great variety of stabilizers are known in the art for stabilizing a diversity of substrates. Their effectiveness varies depending upon the causes of degradation and the substrate stabilized. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

Various silylated hindered phenols have been disclosed in the prior art. For example, mono-hydroxyphenyl-silanes having oxy substituents are disclosed as antioxidants and polymerization inhibitors in Japan Kokai 60-245,653 and 61-100,587. Dimethyl-bis(di-tert-.butylhydroxybenzyloxy)silanes are disclosed in Soviet Union No. 1196-366 as antioxidants for butyl rubbers.

It has now been determined that the compounds of this invention exhibit a variety of desirable properties which makes them particularly effective and useful as stabilizers. Thus, the compounds serve to protect various substrates such as polyolefins, elastomers and lubricating oils against the adverse effects of oxidative and thermal degradation. They are most effective as process stabilizers in polyolefin compositions which may contain metal salts of fatty acids and which also contain a phenolic antioxidant. Thus, they serve to substantially reduce color formation resulting from the presence of the phenolic antioxidant and/or from the processing conditions as well as to directly protect the polymer from said processing conditions.

It is the primary object of this invention to provide a class of novel silane derivatives which exhibits a broad range of improved stabilization performance characteristics.

It is further object to provide compositions of organic materials stabilized against oxidative, thermal and actinic degradation by the presence theein of said derivatives.

Various other objects and advantages of this invention will become evident from the following description thereof.

The compounds of this invention correspond to the formula

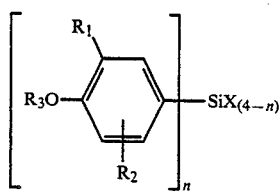

wherein
n is an integer from 2-4;
$R_1$, $R_2$ and X are independently hydrogen, $C_1$-$C_{18}$ alkyl, $C_5$-$C_{12}$ cycloalkyl, phenyl, phenyl substituted by alkyl of 1 to 18 carbon atoms, $C_7$-$C_9$ aralkyl or said aralkyl substituted by alkyl of 1 to 18 carbon atoms; and X is also halogen or hydroxy; and $R_3$ is hydrogen or —Si($R_4$)($R_5$)($R_6$) with $R_4$, $R_5$ and $R_6$ being independently $C_1$-$C_4$ alkyl or phenyl.

Preferred compounds within the above structure are those wherein both $R_1$ and $R_2$ are in the ortho position to the $OR_3$ group. The $R_1$ and $R_2$ groups are preferably straight-chain or branched alkyl with 1 to 8 carbon atoms, such as methyl, n-butyl, sec-butyl, tert-butyl, tert-pentyl, 2-ethylhexyl, n-octyl and 1,1,3,3-tetramethylbutyl. The groups methyl, tert-butyl, tert-pentyl and 1,1,3,3-tetramethylbutyl are especially preferred. Also especially preferred, as previously noted, is for the $R_2$ group to be in the ortho position to the $OR_3$ group, particularly if $R_2$ is tert-alkyl.

When $R_1$, $R_2$ and X are cycloalkyl, they include cyclopentyl or cyclohexyl and when they are aralkyl, they represent benzyl, alpha-methybenzyl or alpha, alpha-dimethylbenzyl.

Other preferred substituents are n as 2 or 3, X as hydrogen, hydroxy, methyl or phenyl and $R_3$ as hydrogen or trimethylsilyl.

The derivatives of this invention wherein $R_3$ is the silylated radical can be prepared by reacting the appropriately substituted brominated silane of the formula

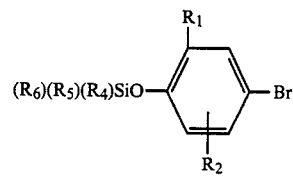

with the appropriately substituted halosilane in a solvent to yield the desired product. Typical halosilanes include dichlorodimethylsilane, dichloromethylsilane, dichlorodiphenylsilane and silicon (IV) chloride, among others. The solvent is preferably a heterocyclic ether such as tetrahydrofuran. The reaction temperature ranges from −78° C. to 30° C. The reaction is also conducted in the presence of an organometallic base such as n-butyllithium, sec-butyllithium or tert-butyllithium or n-butyllithium plus N,N,N',N'-tetramethylethylenediamine. Corresponding organometallic bases of sodium or potassium are also contemplated as useful for this purpose.

The corresponding hydroxyphenyl-silanes can be prepared by hydrolyzing the above noted product utilizing a deprotecting agent such as tetrabutylammonium fluoride trihydrate, dilute sodium hydroxide solution, water alone or low molecular weight alcohols. This reaction is likewise conducted in a solvent such as tetrahydrofuran. The starting materials needed to prepare the stabilizers of this invention are items of commerce or can be prepared by known methods.

The compounds of the present invention are particularly effective in stabilizing organic materials subject to oxidative, thermal and actinic degradation, such as plastics, polymers and resins.

Substrates in which these compounds are particularly useful are polyolefins such as polyethylene and polypropylene; polystyrene, including impact polystyrene, ABS resin, SBR, isoprene, as well as natural rubber, polyesters including polyethylene terephthalate and polybutylene terephthalate, including copolymers, and lubricating oils such as those derived from mineral oil.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylo-nitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of arboxylated styrene/butadiene copolymers.

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants
1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol
1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol
1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)
1.4. Alkylidene-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethybenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane
2,6-di-(3-tert.butyl-5-methyl-2-hydroxybenzyl)-4-methylphenol phenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrate]
di-(3-tert.butyl-4-hydroxy-5-methylphenyl)-dicyclopentadiene diene
di-[2-(3'-tert.butyl-2'-hydroxy-5'-methyl-benzyl)-6-tert.butyl-4-methylphenyl]-terephthalate.
1.5. Benzyl compounds, for example,
1,3,5-tri-(3,5-di-tert.butyl-4-hydroxybenzyl)-2,4,6-trimethylbenzene-di-(3,5-di-tert.butyl-4-hydroxybenzyl)-sulfide
3,5-di-tert.butyl-4-hydroxybenzyl-mercapto-acetic acid isooctyl ester
bis-(4-tert.butyl-3-hydroxy-2,6-dimethylbenzyl)dithiol-terephthalate
1,3,5-tris-(3,5-di-tert.butyl-4-hydroxybenzyl)-isocyanurate
1,3,5-tris-(4-tert.butyl-3-hydroxy-2,6-dimethylbenzyl)-isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt
1.6. Acylaminophenols, for example
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenyl)-carbamate
1.7. Esters of β-(3,5-di-tert-butyl-4-hydroxyphenyl)-propionic acid with monohydric or polyhydric alcohols, for example,
methanol
diethyleneglycol
octadecanol
triethyleneglycol
1,6-hexanediol
pentaerythritol
neopentylglycol
tris-hydroxyethyl isocyanurate
thiodiethyleneglycol
di-hydroxyethyl oxalic acid diamide
1.8. Esters of β-(5-tert-butyl-4-hydroxy-3-methylphenyl)-propionic acid with monohydric or polyhydric alcohols, for example,
methanol
diethyleneglycol
octadecanol
triethyleneglycol
1,6-hexanediol
pentaerythritol
neopentylglycol
tris-hydroxyethyl isocyanurate
thiodiethyleneglycol
di-hydroxyethyl oxalic acid diamide
1.9. Amides of β-(3,5-di-tert.butyl-4-hydroxyphenyl)-propionic acid for example,
N,N'-di-(3,5-di-tert.butyl-4-hydroxyphenylpropionyl)-hexamethylenediamine
N,N'-di-(3,5-di-tert.butyl-4-hydroxyphenylpropionyl)-trimethylenediamine
N,N'-di-(3,5-di-tert.butyl-4-hydroxyphenylpropionyl)-hydrazine 2. UV absorbers and light stabilizers 2.1. 2-(2'-Hydroxyphenyl)-benzotriazoles, for example, the 5'-methyl-, 3',5'-di-tert.butyl-, 5'-tert.butyl-, 5'-(1,1,3,3-tetramethylbutyl)-, 5-chloro-3',5'-di-tert.-butyl-, 5-chloro-3'-tert.butyl-5'-methyl-, 3'-sec.butyl-5'-tert.butyl-, 4'-octoxy, 3',5'-di-tert.amyl-, 3',5'-bis-(α,α-dimethylbenzyl)-derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivative.

2.3. Esters of optionally substituted benzoic acids for example, phenyl salicylate, 4-tert.butyl-phenylsalicylate, octylphenyl salicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.butylphenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclo-hexyl-di-ethanolamine, nickel dibutyldithiocarbamate, nickel salts of 4-hydroxy-3,5-di-tert.butyl-benzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate, bis-(1,2,2,6,6-pentamethylpiperidyl)-sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert.octylamino-2,6-dichloro-1,3,5-s-triazine, tris-2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-dioctyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis (3-dimethylaminopropyl)oxalamide, 2-ethoxy-5-tert.butyl-2'-ethyloxanilide and its mixture with 2-ethoxy-2'-ethyl-5,4'-di-tert.butyl-oxanilide and mixtures of ortho- and para-methoxy-as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert.butylphenyl) phosphite, di-isodecylpentaerythritol diphosphite, di-(2,4-di-tert.butylphenyl)pentaerythritol diphosphite, tristearylsorbitol triphosphite, tetrakis-(2,4-di-tert.butylphenyl)-4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black, graphite.

10. Other additives, for example, plasticizers, lubricants, emulsifiers, pigments, optical brighteners, flame-proofing agents, anti-static agents, blowing agents and thiosynergists such as dilaurylthiodipropionate or distearylthiodipropionate.

Still another group of coadditives which can be advantageously used in conjunction with the instant (hydroxyphenyl)silanes are the hydroxylamines such as the N,N-dialkylhydroxylamines and the N,N-diaralkylhydroxylamines. Examples of such hydroxylamines include the N,N-dialkylhydroxylamines with alkyl of 1 to 18 carbon atoms, preferably alkyl of 8 to 18 carbon atoms; and N,N-dibenzylhydroxylamine and substituted N,N-dibenzylhydroxylamines where the benzyl moiety is substituted by alkyl of 1 to 12 carbon atoms or by alpha,alpha-dimethylbenzyl.

A preferred composition of the instant invention additionally contains an effective stabilizing amount of a phenolic antioxidant. Preferably such phenolic antioxidants include n-octadecyl 3,5-di-tert-butyl-4-hydroxyhydrocinnamate, neopentanetetrayl tetrakis-(3,5-di-tert-butyl-4-hydroxyl-hydrocinnamate), di-n-octadecyl 3,5-di-tert-butyl-4-hydroxybenzyl-phosphonate, 1,3,5-tris-(3,5-di-tert-butyl-4-hydroxy-benzyl)isocyanurate, thiodiethylene bis(3,5-di-tert-butyl-4-hydroxyhydrocinnamate), 1,3,5-trimethyl-2,4,6-tris (3,5-di-tert-butyl-4-hydroxybenzyl)-benzene, 3,6-di-oxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-di-methyl-4-tert-butyl-3-hydroxybenzyl)-isocyanurate, 1,1,3-tris-(2-methyl-4-hydroxy-5-tert-butylphenyl)-butane, 1,3,5-tris-[2-(3,5-di-tert-butyl-4-hydroxy-hydrocinnamoyloxy)-ethyl]-isocyanurate, 3,5-di-(3,5-di-tert-butyl-4-hydroxybenzyl)-mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl-3,5-di-tert-butyl-4-hydroxybenzylphosphonate), ethylene bis[3,3-di(3-tert-butyl-4-hydroxyphenyl)butyrate], octyl 3,5-di-tertbutyl-4-hydroxybenzylmercaptoacetate, bis(3,5-di-tert-butyl-4-hydroxyhydrocinnamoyl)hydrazide, and N,N'-bis-[2-(3,5-tert-butyl-4-hydroxyhydroxo-cinnamoyloxy)ethyl]-oxamide, and preferably neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris-(3,5-di-tert-butyl-4-hydroxybenzyl)isocyanurate, 2,6-di-tert-butyl-p-cresol or 2,2'-ethylidene-bis(4,6-di-tert-butylphenol).

The following examples illustrate the embodiments of this invention. In these examples, allparts given are by weight unless otherwise specified.

EXAMPLE 1

Dimethyl-bis[3,5-di-tert-butyl-4-trimethylsilyloxyphenyl]-silane silane

A suspension of 5.0 g (14 mmol) of 4-bromo-2,6-di-tert-butylphenoxy (trimethyl)silane in 20 ml of tetrahydrofuran at −78° C. is admixed in dropwise fashion with 8.75 ml (0.9 g, 14 mmol) of a 1.6 molar solution of n-butyllithium in hexane. The homogeneous reaction mixture is stirred for 15 minutes and to it is added 0.8 g (7 mmol) of dichlorodimethylsilane. The reaction mixture is filtered to remove lithium chloride and the solvent is removed in vacuo from the filtrate. The residue is dissolved in 50 ml of chloroform and is extracted (2×25 ml) with water. The organic phase is dried over anhydrous sodium sulfate and the solvent is removed in vacuo. The residue is recrystallized from heptane to give 1.5 g (33%) of product as white crystals; mp. 173°–174° C.

Anal. Calcd. for $C_{36}H_{64}O_2Si_3$: C, 70.5; H, 10.5. Found: C, 70.2; H, 10.8.

EXAMPLE 2

Dimethyl-bis(3,5-di-tert-butyl-4-hydroxyphenyl)silane

To a solution of 9.8 g (16 mmol) of dimethylbis(3,5-di-tert-butyl-4-trimethylsilyloxyphenyl)silane in 50 ml of tetrahydrofuran is slowly added 10.6 g (32 mmol) of tetrabutylammonium fluoride trihydrate. The reaction mixture is stirred for 1 hour at room temperature and to it is added 0.8 g (14 mmol) of glacial acetic acid. The reaction mixture is poured into 250 ml of water and the solution is extracted (2×125 ml) with methylene chloride. The organic phase is dried over anhydrous sodium sulfate and the solvent is removed in vacuo to give 7.3 g of an orange residue which crystallizes on standing. The residue is recrystallized from heptane to give 1.2 g (17%) of a white solid; mp. 186°–188° C.

Anal. Calcd. for $C_{30}H_{48}O_2Si$: C, 76.9; H, 10.3. Found: C, 77.2; H, 10.7.

EXAMPLE 3

Diphenyl-bis(3,5-di-tert-butyl-4-trimethylsilyloxyphenyl)silane

To a suspension of 20.0 g (56 mmol) of 4-bromo-2,6-di-tert-butylphenoxy-(trimethyl)silane in 100 ml of tetrahydrofuran at −78° C. is added dropwise 35 ml (3.6 g, 56 mmol) of a 1.6 molar solution of n-butyllithium in hexane. The homogeneous reaction mixture is stirred for 30 minutes at −78° C. and to it is added 7.1 g (28 mmol) of dichlorodiphenylsilane. The solvent is removed in vacuo from the reaction mixture. The residue is placed in 500 ml of diethylether and filtered to remove lithium chloride. The filtrate is dried over anhydrous sodium sulfate and the solvent is removed in vacuo to give 22.0 g of a colorless liquid. The crude product is purified by preparative HPLC (Silica gel, 1:1, heptane:methylene chloride eluent) to give 5.0 g (24%) of product as yellow crystals; mp. 100°–115° C.

Anal. Calcd. for $C_{46}H_{68}O_2Si_3$: C, 74.9; H, 9.3. Found: C, 74.5; H, 9.5.

EXAMPLE 4

Diphenyl-bis(3,5-di-tert-butyl-4-hydroxyphenyl)silane

To a solution of 5.0 g (7 mmol) of diphenylbis(3,5-di-tert-butyl-4-trimethylsilyloxyphenyl)silane in 30 ml of tetrahydrofuran at 0° C. is added dropwise a solution of 4.3 g (14 mmol) of tetrabutylammonium fluoride trihydrate in 35 ml of tetrahydrofuran. The reaction mixture is stirred for 5 minutes at 0° C. and to it is added dropwise a solution of 2.2 g (62 mmol) of concentrated hydrochloric acid in 10 ml of tetrahydrofuran. The solvent is removed in vacuo and to the residue is added 250 ml of diethylether. The solution is extracted (3×100 ml) with water. The organic phase is dried over anhydrous sodium sulfate and the solvent is removed in vacuo to give 4.0 grams of a white solid. The crude product is recrystallized from heptane to give 3.0 g (75%) of product as white crystals; mp. 193°–194.5° C.

Anal. Calcd. for $C_{40}H_{52}O_2Si$: C, 81.0; H, 8.3. Found: C, 81.1; H, 8.7.

EXAMPLE 5

Methyl-bis(3,5-di-tert-butyl-4-trimethylsilyloxyphenyl)silane

To a suspension of 20.0 g (56 mmol) of 4-bromo-2,6-di-tert-butylphenoxy (trimethyl)silane in 100 ml of tetrahydrofuran at −78° C. is added dropwise 35 ml (3.6 g, 56 mmol) of a 1.6 molar solution of n-butyllithium in hexane. The homogeneous reaction mixture is stirred for 30 minutes at −78° C. and to it is added 3.2 g (28 mmol) of dichloromethylsilane. The solvent is removed in vacuo from the reaction mixture. To the residue is added 500 ml of diethylether and the mixture is filtered to remove lithium chloride. The solvent is removed in vacuo from the filtrate and the residue is recrystallized from acetonitrile to give 12.5 grams (75%) of product as an off-white solid; mp. 119°–121° C.

Anal. Calcd. for $C_{35}H_{62}O_2Si_3$: C, 70.2; H, 10.4. Found: C, 69.3; H, 10.5.

EXAMPLE 6

Methyl-bis(3,5-di-tert-butyl-4-hydroxyphenyl)silane

To a solution of 6.0 g (10 mmol) of methylbis (3,5-di-tert-butyl-4-trimethylsilyloxyphenyl)silane in 30 ml of tetrahydrofuran is added dropwise a solution of 6.3 g (20 mmol) of tetrabutylammonium fluoride trihydrate in 35 ml of tetrahydrofuran. A vigorous evolution of gas is witnessed during the addition and the reaction mixture becomes green in color. The reaction mixture is stirred for 5 minutes at room temperature and to it is added dropwise a solution of 1.9 g (52 mmol) of concentrated hydrochloric acid in 10 ml of tetrahydrofuran. The solvent is removed in vacuo and the residue is recrystallized from n-propyl alcohol to give 2.7 grams of white solid which is a mixture of two products. The product mixture is separated by preparative HPLC (silica gel, 99:1, heptane, ethyl acetate) to give 0.4 g (9%) of the desired product as white crystals; mp. 191°–193.5° C.

Anal. Calcd. for $C_{29}H_{46}O_2Si$: C, 76.6; H, 10.2. Found: C, 76.7; H, 10.2.

EXAMPLE 7

Methyl-bis(3,5-di-tert-butyl-4-hydroxyphenyl)fluorosilane

Methyl-bis(3,5-di-tert-butyl-4-hydroxyphenyl)fluorosilane is isolated by preparative HPLC (silica gel, 99:1, heptane, ethyl acetate eluent) during the purification of methyl-bis(3,5-di-tert-butyl-4-hydroxyphenyl)silane (Example 6) as 0.5 grams of a white solid; mp. 185°–188° C.

Anal. Calcd. for $C_{29}H_{45}FO_2Si$: C, 73.7; H, 9.6; F, 4.0. Found: C, 73.9; H, 9.8; F, 3.6.

EXAMPLE 8

Tris(3,5-di-tert-butyl-4-trimethylsilyloxyphenyl)hydroxysilane

To a suspension of 20.0 g (56 mmol) of 4-bromo-2,6-di-tert-butylphenoxy (trimethyl)silane in 100 ml of tetrahydrofuran at −78° C. is added dropwise 35 ml (3.6 g, 56 mmol) of a 1.6 molar solution of n-butyllithium in hexane. The homogeneous reaction mixture is stirred for 30 minutes and to it is added 2.4 g (14 mmol) of silicon (IV) chloride. The solvent is removed in vacuo from the reaction mixture. To the residue is added 300 ml of dichloromethane and the mixture is extracted (3×150 ml) with water. The organic phase is dried over anhydrous sodium sulfate and the solvent is removed in vacuo to give 17.1 g of a red syrup. The crude product is purified by preparative HPLC (silica gel, 96.4, heptane, ethyl acetate eluent) to give 2.8 g (22%) of product as a white solid; mp. 192°–196° C.

Anal. Calcd. for $C_{51}H_{88}O_4Si_4$: C, 69.8; H, 10.1. Found: C, 70.3; H, 10.3.

EXAMPLE 9

Tris(3,5-di-tert-butyl-4-hydroxyphenyl)hydroxysilane

To a stirred solution of 0.40 g (0.45 mmol) of tris-(3,5-di-tert-butyl-4-trimethylsilyloxyphenyl)hydroxysilane in 3 ml of tetrahydrofuran at 0° C. is added dropwise a solution of 0.43 g (1.37 mmol) of tetrabutylammonium fluoride trihydrate in 3 ml of tetrahydrofuran. The reaction mixture is stirred for 5 minutes at 0° C. and to it is added dropwise a solution of 0.19 g of concentrated hydrochloric acid in 1 ml of tetrahydrofuran. The solvent is removed in vacuo and the residue is dissolved in 30 ml of diethylether. The solution is extracted (3×25 ml) with water. The organic phase is dried over anhydrous sodium sulfate and the solvent is removed in vacuo to give 0.29 g of a white amorphous solid. The crude product is purified by preparative thin layer chromatography (silica gel, 7:3, heptane:ethyl acetate eluent) followed by crystallization from a heptane/toluene solvent mixture to give 0.14 g (46%) of product as a white solid; mp. 257°–258° C.

Anal. Calcd. for $C_{42}H_{64}O_4Si$: C, 76.3; H, 9.8. Found: C, 75.9; H, 9.8.

EXAMPLE 10

This example illustrates the thermal stabilizing effectiveness of the instant stabilizers.

| Base | Formulation |
| --- | --- |
| Polypropylene* | 100 parts |
| Calcium Stearate | 0.10 parts |

*Profax 6501 from Himont

Stabilizers are solvent blended into polypropylene as solutions in methylene chloride and after removal of the solvent by evaporation at reduced pressure, the resin is extruded using the following extruder conditions:

| | Temperature (°C.) |
| --- | --- |
| Cylinder #1 | 232 |
| Cylinder #2 | 246 |
| Cylinder #3 | 260 |
| Die #1 | 260 |
| Die #2 | 260 |
| Die #3 | 260 |
| RPM | 100 |

The melt flow rate (MFR) is determined by ASTM method 1238 condition L. The melt flow rate is a measure of the molecular weight for a specific type of polymer. The results are shown below.

| | | MFR (g/10 min.) After Extrusion | |
| --- | --- | --- | --- |
| Additive | Conc. (% by wt.) | 1 | 5 |
| None | — | 4.4 | 11.5 |
| Compound of Example 2 | 0.1 | 2.6 | 4.4 |

Summarizing, it is seen that this invention provides organic materials stabilized against degradation by the presence therein of various novel silanes. Variations may be made in proportions, procedures and materials without departing from the scope of the invention as defined by the following claims.

What is claimed is:

1. A compound of the formula

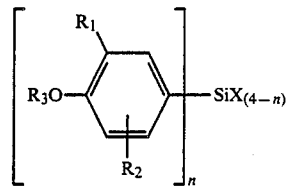

wherein n is an integer from 2–4;

$R_1$, $R_2$ and X are independently hydrogen, $C_1$–$C_{18}$ alkyl, $C_5$–$C_{12}$ cycloalkyl, phenyl, phenyl substituted by alkyl of 1 to 18 carbon atoms, $C_7$–$C_9$ aralkyl or said aralkyl substituted by alkyl of 1 to 18 carbon atoms; and X is also halogen or hydroxy; and $R_3$ is hydrogen or —Si($R_4$)($R_5$)($R_6$) with $R_4$, $R_5$ and $R_6$ being independently $C_1$–$C_4$ alkyl or phenyl.

2. The compound of claim 1, wherein $R_1$ and $R_2$ are alkyl of from 1 to 8 carbon atoms.

3. The compound of claim 2, wherein $R_1$ and $R_2$ are tert-butyl.

4. The compound of claim 1, wherein $R_2$ is in the ortho position to the $OR_3$ group.

5. The compound of claim 1, wherein n is 2 or 3 and X is hydrogen, hydroxy, methyl or phenyl.

6. The compound of claim 1, wherein $R_3$ is hydrogen or trimethylsilyl.

7. Dimethyl-bis[3,5-di-tert-butyl-4-trimethylsilyloxyphenyl]silane according to claim 1.

8. Dimethyl-bis(3,5-di-tert-butyl-4-hydroxyphenyl)silane according to claim 1.

9. Diphenyl-bis(3,5-di-tert-butyl-4-trimethylsilyloxyphenyl)silane according to claim 1.

10. Diphenyl-bis(3,5-di-tert-butyl-4-hydroxyphenyl)silane according to claim 1.

11. Methyl-bis(3,5-di-tert-butyl-4-trimethylsilyloxyphenyl)silane according to claim 1.

12. Methyl-bis(3,5-di-tert-butyl-4-hydroxyphenyl)silane according to claim 1.

13. Methyl-bis(3,5-di-tert-butyl-4-hydroxyphenyl)fluorosilane according to claim 1.

14. Tris(3,5-di-tert-butyl-4-trimethylsilyloxyphenyl)hydroxysilane according to claim 1.

15. Tris(3,5-di-tert-butyl-4-hydroxyphenyl)hydroxysilane according to claim 1.

16. A composition of matter comprising an organic material subject to oxidative, thermal and actinic degradation stabilized with an effective stabilizing amount of a compound of claim 1.

17. The composition of claim 16, wherein the organic material is a synthetic polymer.

18. The composition of claim 17, wherein te synthetic polymer is a polyolefin homopolymer or copolymer.

19. The composition of claim 16 which also contains a phenolic antioxidant.

20. A method for stabilizing an organic material against oxidative, thermal and actinic degradation which comprises incorporating into said organic material an effective stabilizing amount of a compound of claim 1.

* * * * *